United States Patent [19]

Greenberg et al.

[11] Patent Number: 5,096,417
[45] Date of Patent: Mar. 17, 1992

[54] ORTHODONTIC VISUAL ENHANCEMENT METHOD

[76] Inventors: Michael H. Greenberg, 8535 Tanglewood Sq., Chagrin Falls, Ohio 44022; Richard S. Arnstine, 20620 N. Park Blvd., Shaker Heights, Ohio 44118

[21] Appl. No.: 669,653

[22] Filed: Mar. 14, 1991

[51] Int. Cl.$^5$ .............................................. A61C 3/00
[52] U.S. Cl. ............................................ 433/24; 433/9
[58] Field of Search ................................. 433/8, 9, 24

[56] References Cited

U.S. PATENT DOCUMENTS 4,592,141  8/1990  Wool ...................................... 433/8

Primary Examiner—John J. Wilson
Attorney, Agent, or Firm—Pearne, Gordon, McCoy & Granger

[57] ABSTRACT

A method for visually highlighting the structural features of orthodontic appliances to facilitate easy discernment of difficult-to-see features, thereby simplifying and reducing the time required for therapeutic readjustment of orthodontic appliances, is disclosed, wherein a contrasting coloring agent is applied directly to the orthodontic appliances to achieve the desired results without any accompanying undesirable effects or disadvantages.

8 Claims, 2 Drawing Sheets

ORTHODONTIC VISUAL ENHANCEMENT METHOD

BACKGROUND OF THE INVENTION

The invention relates to a method for highlighting the structural features of orthodontic appliances, which allows dentists to easily discern the structural features of the orthodontic brackets and the position of the brackets on the teeth to which they are affixed. The invention also concerns a delivery system for applying a coloring or contrast-inducing agent to and between the surfaces of orthodontic brackets.

DESCRIPTION OF THE PRIOR ART

For cosmetic reasons, and to minimize patient discomfort, orthodontic appliances are generally made as small as is practically possible. Orthodontic appliances, which had previously been constructed almost exclusively from metal alloys, are now being fabricated from natural tooth-colored material such as porcelain or sapphire materials or plastics. These natural-colored appliances, because of their innocuous appearance, are becoming increasingly popular with patients. Orthodontists, however, find it more difficult to discern the features of these small natural tooth-colored appliances since they provide very little visual contrast between the natural tooth-colored appliances and the patient's white teeth.

A substantial amount of an orthodontist's time is spent readjusting the orthodontic wires on the brackets to progressively modify the mechanical forces being applied to the brackets during continuing therapy. Because of the nature of orthodontic work and the difficulty in seeing the natural tooth-colored brackets, the orthodontist must spend considerably more time adjusting the wires on the natural-colored brackets than was previously required with the metal alloy brackets. In addition, the orthodontist may experience eye strain and fatigue during the daily routine of numerous office visits. As a result, the orthodontist may not be able to schedule as many patients during a day, and he or she may need to limit his or her practice to fewer patients as natural-colored appliances become more popular, with a consequent reduction in income.

To overcome the problem of visibility of the small, non-contrasting orthodontic components, a variety of techniques have been developed to increase visibility during initial installation of the orthodontic appliances. Brackets have been marked on certain surfaces with colored dots and other indicators to indicate the direction of torque or to help the dentist differentiate right-sided, left-sided, upper and lower brackets. Removable color-coded long axis indicators have been provided by Unitek Corporation in its "Transcend" brane brackets for giving a positive placement reference for the axis, with each tooth having its own color code for easy selection and identification. Color-coded identification marks have also been cast into brackets. Ormco Corporation has made color-coded vertical and horizontal placement caps for its "GEM" brand brackets and also has made metal brackets with color-coded placement-/identification caps for specific teeth and with different vertical displacements.

U.S. Pat. No. 4,952,141 discloses a removable marker in the slot of an orthodontic bracket. The marker, which facilitates visual alignment of the brackets during their initial installation, must be either brushed or scraped out of the slot after the bracket has been cemented to a tooth.

These conventional techniques are generally employed only during the initial installation of orthodontic appliances and are of no value during the numerous adjustments which are required during the course of therapy. In addition, practicing orthodontists often find these conventional techniques to be more difficult to use than is desired.

SUMMARY OF THE INVENTION

Accordingly, it is an object of the present invention to provide a simple method of applying a coloring agent to teeth and to the orthodontic brackets on the teeth to impart contrast to the surfaces and edges of the orthodontic brackets so that orthodontists can more easily discern the orthodontic appliances.

A further object of the invention is to provide an effective contrasting agent which when applied to the teeth and orthodontic brackets will allow orthodontists to more easily adjust the orthodontic appliances during the stages of continuing therapy.

A still further object of the invention is to provide a coloring agent which is easily removable after its application, and which has no long-lasting effects.

These and other objects of the invention will be apparent from the following specification.

The objects of the invention are achieved by the direct application of food coloring to the installed orthodontic brackets. Any of a variety of food coloring agents may be used, and those having FDA approval are preferred, since they have already been proven to the non-toxic and safe for use in a patient's mouth, and do not require any further regulatory approval. Additionally, the coloring agent should provide visual contrast to the orthodontic appliances and effectively highlight the edges and corners of orthodontic appliances to provide visual discernment of the features thereof. Another important characteristic of the coloring agent is that it be resistant to absorption by the teeth and the orthodontic brackets.

The coloring agent is applied directly to the installed orthodontic appliance at the beginning of a therapeutic session, preferably with a single use applicator having a small reservoir of coloring agent associated therewith. The orthodontist then allows the coloring agent to disperse onto and accumulate at the edges, corners and level surfaces of the brackets through a combination of cohesive, adhesive and gravity forces. The coloring agent provides excellent contrast and easy discernment of the structural features of the orthodontic appliances. The orthodontist should remove the coloring agent before any significant absorption of the coloring agent into the teeth or brackets has occurred during the course of therapy. Using the preferred coloring agent, it has been found that the coloring agent may be left on for a period of approximately five minutes. The coloring agent has no lingering or residual effects and can be easily removed at the conclusion of therapy. Typically, the coloring agent may be removed by simply applying a stream or jet of water into the patient's mouth.

The method of the invention, therefore, provides a safe, simple procedure having no harmful side effects or disadvantages, which visually highlights features of orthodontic appliances, thereby reducing the time required to make adjustments to the orthodontic appliances, and benefitting both the orthodontist and the patient.

DETAILED DESCRIPTION OF THE INVENTION

Although the invention may be used at the initiation of orthodontic therapy, it is generally directed to subsequent visits during the course of continuing therapy after installation-markers, if originally present, have been removed from the orthodontic appliances. During these subsequent visits, the orthodontist will generally be changing the wires, and/or adjusting the wires and brackets. According to the invention, a coloring agent is applied directly to the orthodontic appliances at the beginning of each visit to help the orthodontist with the visual perception of natural tooth-colored enamel or porcelain brackets and/or other non-contrasting, low visibility orthodontic appliances which may be used currently or in the future, such as natural tooth-colored orthodontic wires.

Figure 1:
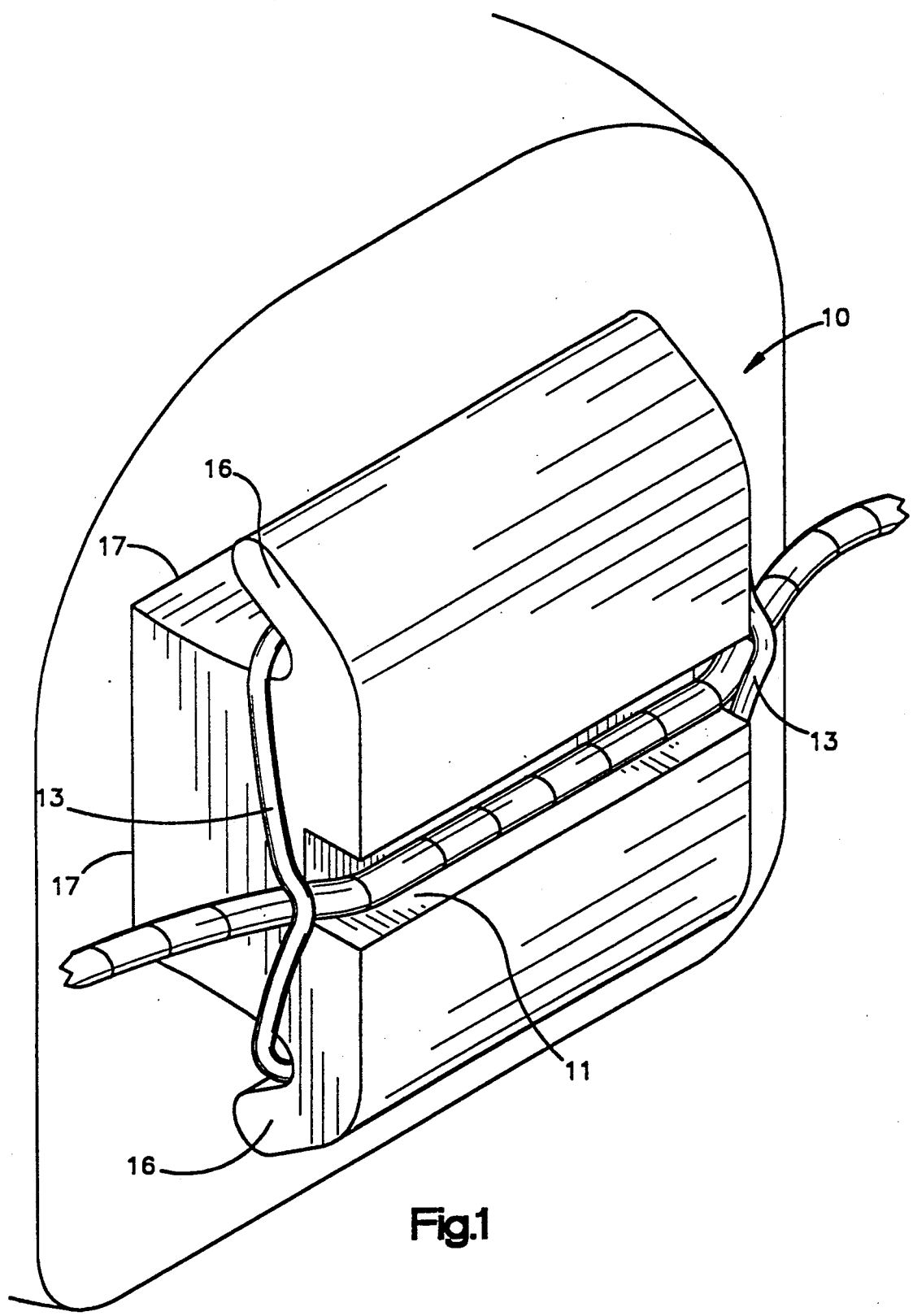
FIG. 1 is a perspective view of a typical orthodontic bracket mounted to a tooth.

In particular, as shown in FIG. 1, the process helps the orthodontist see the alignment of slot 11 in a bracket 10, which are used to receive and retain a wire 12, and to see the bracket tie wings 16. In addition, the peripheral edges 17 of the bracket are highlighted.

Natural tooth-colored wires corresponding to the wire 12 are being developed and may be available in the near future. It is anticipated that these natural tooth-colored wires may, like the natural tooth-colored brackets, become very popular with patients. The inventive process herein described may be of even greater assistance to orthodontists when natural tooth-colored wires are used.

The method of this invention relies primarily on surface tension between the appliances and the coloring agent to preferentially distribute the colorant to the corners and edges of intersecting surfaces. The surface tension causes the coloring agent to accumulate on level surfaces and to accumulate on bottom surfaces because of adhesive forces.

It is believed that higher cohesive forces relative to the adhesive forces cause the colorant to roll off most of the inclined surfaces of the bracket, but that the adhesive forces are sufficient to retain colorant which accumulates at edges and corners where multiple surfaces intersect. In particular, the coloring agent may tend to accumulate within the slot 11 in the bracket and around the peripheral edges 17 where the bracket meets the surface of the tooth. The coloring agent also helps to highlight and visually define other features of the bracket. While the precise phenomena responsive for achieving the results of the invention may not be completely understood, the means for achieving the results are fully disclosed herein.

Alternatively, if the coloring agent is simply wiped across the brackets and teeth, the coloring agent will accumulate on the front surfaces of the bracket but will not substantially accumulate in the slot 11, leaving the slot well defined by the absence of coloring.

In accordance with the invention, highly adsorptive colorants and prolonged exposure of the colorant to the teeth and the orthodontic appliances should be avoided. After applying the colorant to the orthodontic appliances, the orthodontist should allow the colorant to enter into the corners and edges before making adjustments to the wires. The colorant also helps to identify the elastic bumpers 13 which go around the brackets and hold the wire to the brackets.

The coloring agent for use in accordance with the invention should be non-toxic and non-hazardous, and should preferably be a water-soluble, FDA-approved food coloring. FDA-approved food colorings are preferred because they do not require any additional regulatory approval and are known to be safe for oral use.

An important feature of the invention is that the coloring agent should be easily removable. Therefore, it is important that the coloring agent be substantially incapable of being absorbed by the teeth and the orthodontic appliances. The coloring agent should preferably be a color such as green or blue to provide greater contrast between the coloring agent and the natural tooth-colored background. While a number of coloring agents have been found to be satisfactory, a readily available blue food coloring comprising F.D.&C. Blue NO. 1, diluted with water and propylene glycol, has been found to be suitable.

Almost any effective coloring agent is susceptible to some absorption into the teeth and the orthodontic appliances, but such absorption should be minimized as much as possible. It has been found that the advantages of the present invention can be achieved without substantial absorption of the coloring agent into the teeth and the orthodontic appliances. By avoiding absorption, the coloring agent can also be easily removed. Using the preferred coloring agent, it has been found that the colorant can be left on the teeth and the orthodontic appliances for approximately five minutes without substantial absorption occurring.

Figure 2:
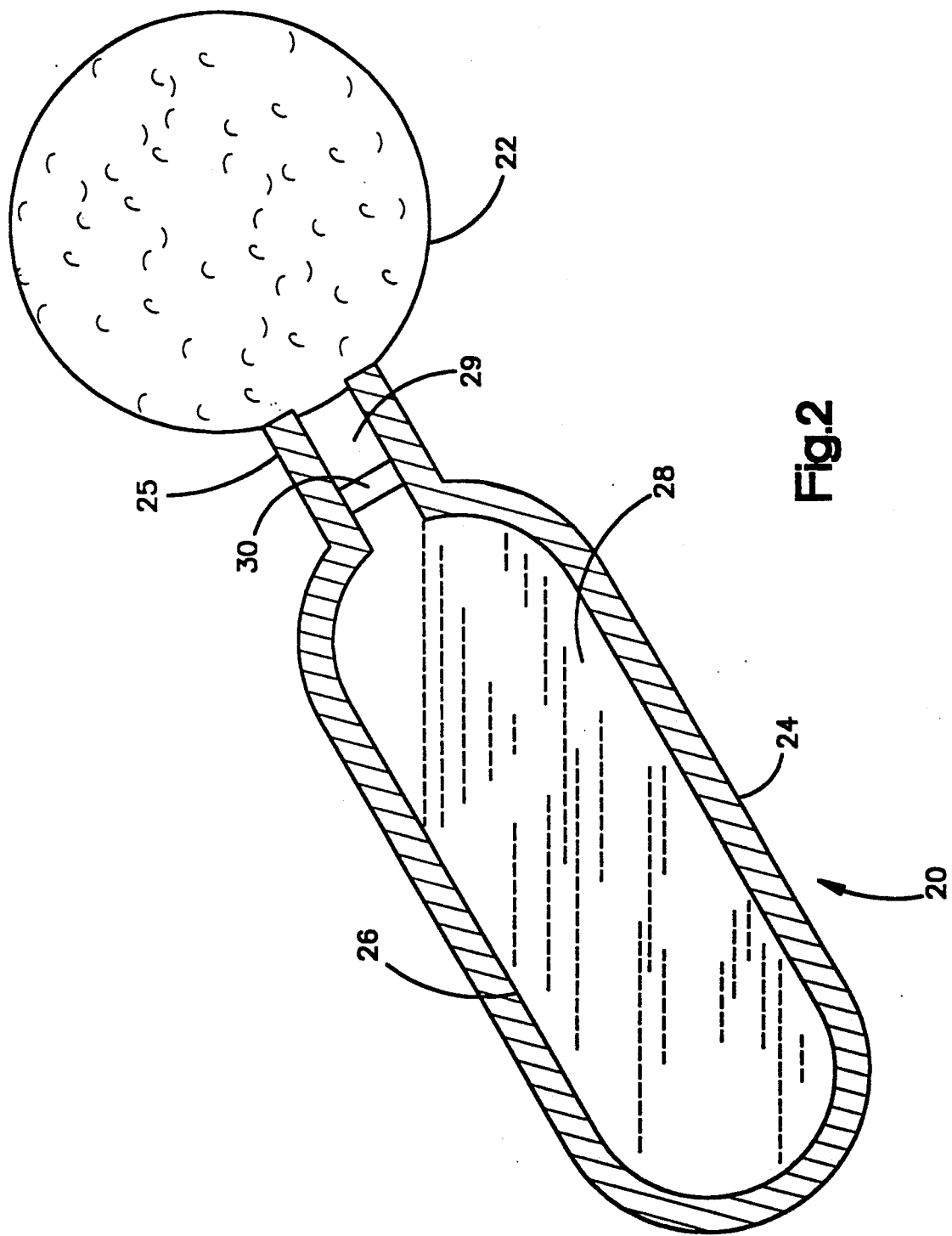
FIG. 2 is a perspective view, with portions broken away for clarity, of a single use applicator for applying a coloring agent to installed orthodontic appliances in accordance with one aspect of the invention.

A variety of devices may be used to apply the coloring agent to the patient's teeth and the orthodontic appliances; however, a single use applicator with a small supply of coloring agent is preferred. One such device is shown in FIG. 2. An applicator 20 includes a foam rubber swab 22 attached to an enlarged plastic handle 24 by means of a flexible neck 25. The handle 24 has an internal reservoir 26 containing a small, predetermined quantity of the coloring agent 28. Between the reservoir 26 and the swab 22 is a passage 29 in the neck 25. The passage 29 has a breakable seal 30 which, when broken, allows the coloring agent 28 to flow from the reservoir 26 to the swab 22. The seal 30 can be broken by bending or squeezing the flexible neck 25. A wick (not shown) which could extend from the breakable seal 30 to the swab 22 may be used to help direct the coloring agent 28 to the swab. The coloring agent is then applied by dabbing the teeth and the orthodontic appliances with the swab 22.

Alternatively, the coloring agent could be applied from a jar or bottle using a small foam brush, perhaps similar to a mascara brush. The coloring agent may be dried onto a foam brush so that the colorant can be used by wetting the brush to release the colorant. Another possible alternative is a dispenser in the form of a brush on the end of an eye dropper. The colorant may also be applied using ophthalmic strips such as those manufactured by Barnes-Hind, Inc. under the trademark FUL-GLO. Such ophthalmic strips have a measured amount of coloring agent dried onto a paper strip. The strip is dipped into water and the end of the strip having the colorant on it is applied directly to the orthodontic brackets.

Because the invention primarily relies on the surface tension of the liquid coloring agent rather than absorption to highlight the edges of brackets, the coloring agent can be easy rinsed off by applying a stream or jet of water into the patient's mouth after orthodontic adjustments have been completed. Occasionally, some brushing such as with a tooth brush may be required to remove the coloring agent completely from the teeth and the brackets. As previously mentioned, the coloring agent should not be left on the teeth and the brackets too long so that substantial absorption does not take place. With the preferred coloring agent, the period of application should be limited to approximately five minutes before removal.

While the invention has been shown and described with respect to a particular embodiment thereof, this is for the purpose of illustration rather than limitation, and other variations and modifications of the specific embodiment herein shown and described will be apparent to those skilled in the art. Accordingly, the patent is not to be limited in scope and effect to the specific embodiment herein nor in any other way that is inconsistent with the extent to which the progress in the art has been advanced by the invention.

What is claimed is:

1. A method for visually highlighting structural features of orthodontic appliances to facilitate visual discernment of the features during therapeutic readjustment of the appliances, comprising the steps of:
    applying to a patient's teeth and to orthodontic appliances installed on the patient's teeth a non-toxic coloring agent; and
    allowing the coloring agent to accumulate at edges, corners, and surface irregularities of the orthodontic appliances so as to highlight said structural features.

2. A method according to claim 1, wherein the applying step includes applying a coloring agent which is resistent to substantial absorption by the teeth and the orthodontic appliances.

3. A method according to claim 2, further including the step of therapeutically readjusting the orthodontic appliances after the allowing step.

4. A method according to claim 3, further including the step of removing the coloring agent after the step of therapeutically readjusting the orthodontic appliance before the coloring agent has been substantially absorbed by the teeth and the orthodontic appliances.

5. A method according to claim 4, wherein the removing step is performed by rinsing the patient's mouth with a stream of water.

6. A method according to claim 1, whereby the coloring agent is applied to the teeth the orthodontic appliances to cause the edges of the orthodontic appliances to become highlighted primarily by surface tension between the coloring agent and the orthodontic appliances.

7. A method according to claim 1, wherein said coloring agent is applied to the orthodontic patient's teeth using a single use applicator having a swab attached to a handle, the handle having a reservoir containing a quantity of the coloring agent, the applicator also having a breakable seal which when broken allows the coloring agent to flow to the swab.

8. A method for visually highlighting structural features of orthodontic appliances to facilitate visual discernment of the features during therapeutic readjustment of the appliances, comprising the steps of:
    applying to a patient's teeth and to orthodontic appliances installed on the patient's teeth a non-toxic coloring agent which is resistent to substantial absorption by the teeth and said orthodontic appliances;
    allowing the coloring agent to accumulate at edges, corners, and surface irregularities of the orthodontic appliances so as to highlight said structural features, said highlighting being caused primarily by surface tension between the coloring agent and the orthodontic appliances;
    then therapeutically readjusting the orthodontic appliances; and
    then removing the coloring agent from the patient's mouth by rinsing with a stream of water before the coloring agent has been substantially absorbed by the teeth and the orthodontic appliances.

* * * * *